(12) United States Patent
Orbay et al.

(10) Patent No.: US 7,563,263 B2
(45) Date of Patent: *Jul. 21, 2009

(54) INTRAMEDULLARY FIXATION DEVICE FOR METAPHYSEAL LONG BONE FRACTURES

(75) Inventors: Jorge L. Orbay, Coral Gables, FL (US); Javier E. Castañeda, Miami, FL (US)

(73) Assignee: Depuy Products, Inc., Warsaw, IN (US)

( * ) Notice: Subject to any disclaimer, the term of this patent is extended or adjusted under 35 U.S.C. 154(b) by 359 days.

This patent is subject to a terminal disclaimer.

(21) Appl. No.: 11/210,593

(22) Filed: Aug. 24, 2005

(65) Prior Publication Data

US 2005/0283154 A1 Dec. 22, 2005

Related U.S. Application Data

(63) Continuation of application No. 10/762,695, filed on Jan. 22, 2004, now abandoned, which is a continuation-in-part of application No. 10/315,787, filed on Dec. 10, 2002, now Pat. No. 6,706,046, which is a continuation-in-part of application No. 10/159,611, filed on May 30, 2002, now Pat. No. 6,730,090.

(51) Int. Cl.
*A61B 17/56* (2006.01)
*A61B 17/58* (2006.01)
*A61F 2/30* (2006.01)

(52) U.S. Cl. ................ 606/64; 606/62; 606/67
(58) Field of Classification Search ............ 606/60, 606/62–64, 69, 70, 280–299
See application file for complete search history.

(56) References Cited

U.S. PATENT DOCUMENTS

| 388,000 A | 8/1888 | Rider |
|---|---|---|
| 472,913 A | 4/1892 | Taylor |
| 1,151,861 A | 8/1915 | Brumback |
| 2,056,688 A | 10/1936 | Peterka et al. |

(Continued)

FOREIGN PATENT DOCUMENTS

CA 2174293 A 10/1997

(Continued)

OTHER PUBLICATIONS

"Advances in distal Radius Fracture Management (D)", transcript of American Academy of Orthopaedic Surgeons 2001 Conf.; pp. 134-151, Feb. 28, 2001 including Article by Matthew D. Putnam MD, "Repair and Rehabilitation of Distal Fractures: The Role of Subchondral Fixation" at pp. 144-147.

(Continued)

*Primary Examiner*—Eduardo C Robert
*Assistant Examiner*—Andrew Yang
(74) *Attorney, Agent, or Firm*—Gordon & Jacobson, PC (57) ABSTRACT

A fracture fixation system includes a device with a plate portion intended to be positioned against an exterior surface of bone and an intramedullary portion. The plate portion includes a plurality of fixed angle holes defining a respective number of axes which are divergent. Fasteners coupled within the fixed angle holes extend to follow the contour of subchondral bone and provide a framework for support for fracture healing.

7 Claims, 8 Drawing Sheets

U.S. PATENT DOCUMENTS

| | | | |
|---|---|---|---|
| 2,500,370 A | 3/1950 | McKibbin |
| 2,526,959 A | 10/1950 | Lorenzo |
| 3,025,853 A | 3/1962 | Mason |
| 3,236,141 A | 2/1966 | Smith |
| 3,645,161 A | 2/1972 | Wesker |
| 3,709,218 A | 1/1973 | Halloran |
| 3,717,146 A | 2/1973 | Halloran |
| 3,741,205 A | 6/1973 | Markolf et al. |
| 3,842,825 A | 10/1974 | Wagner |
| 3,939,498 A | 2/1976 | Lee et al. |
| RE28,841 E | 6/1976 | Allgower et al. |
| 4,011,863 A | 3/1977 | Zickel |
| 4,119,092 A | 10/1978 | Gil |
| 4,135,507 A | 1/1979 | Harris |
| 4,153,953 A | 5/1979 | Grobbelaar |
| 4,169,470 A | 10/1979 | Ender et al. |
| 4,172,452 A | 10/1979 | Forte et al. |
| 4,408,601 A | 10/1983 | Wenk |
| 4,467,793 A * | 8/1984 | Ender .................. 606/62 |
| 4,473,069 A | 9/1984 | Kolmert |
| 4,483,335 A | 11/1984 | Tornier |
| 4,484,570 A | 11/1984 | Sutter et al. |
| 4,488,543 A | 12/1984 | Tornier |
| 4,493,317 A | 1/1985 | Klaue |
| 4,503,847 A * | 3/1985 | Mouradian .............. 606/64 |
| 4,506,662 A | 3/1985 | Anapliotis |
| 4,565,193 A | 1/1986 | Streli |
| 4,651,724 A | 3/1987 | Berentey et al. |
| 4,712,541 A | 12/1987 | Harder et al. |
| 4,733,654 A | 3/1988 | Marino |
| 4,776,330 A | 10/1988 | Chapman et al. |
| 4,794,919 A | 1/1989 | Nilsson |
| 4,800,874 A | 1/1989 | David et al. |
| 4,867,144 A | 9/1989 | Kara et al. |
| 4,915,092 A | 4/1990 | Firica et al. |
| 4,923,471 A | 5/1990 | Morgan |
| 4,955,886 A | 9/1990 | Pawluk |
| 5,006,120 A | 4/1991 | Carter |
| 5,013,314 A | 5/1991 | Firica et al. |
| 5,015,248 A | 5/1991 | Burstein et al. |
| 5,035,697 A | 7/1991 | Frigg |
| 5,041,113 A | 8/1991 | Biedermann et al. |
| 5,057,110 A | 10/1991 | Kranz et al. |
| 5,085,660 A | 2/1992 | Lin |
| 5,127,912 A | 7/1992 | Ray et al. |
| 5,151,103 A | 9/1992 | Tepic et al. |
| 5,190,544 A | 3/1993 | Chapman et al. |
| 5,197,966 A | 3/1993 | Sommerkamp |
| 5,201,733 A | 4/1993 | Etheredge, III |
| 5,275,601 A | 1/1994 | Gogolewski et al. |
| 5,304,180 A | 4/1994 | Slocum |
| 5,352,228 A | 10/1994 | Kummer et al. |
| 5,352,229 A | 10/1994 | Goble et al. |
| 5,356,253 A | 10/1994 | Whitesell |
| 5,356,410 A | 10/1994 | Pennig |
| 5,364,399 A | 11/1994 | Lowery et al. |
| 5,382,248 A | 1/1995 | Jacobson et al. |
| 5,437,667 A | 8/1995 | Papierski et al. |
| 5,458,654 A | 10/1995 | Tepic |
| 5,472,444 A | 12/1995 | Huebner et al. |
| 5,484,438 A | 1/1996 | Pennig |
| 5,486,176 A | 1/1996 | Hildebrand et al. |
| 5,527,311 A | 6/1996 | Procter et al. |
| 5,531,745 A | 7/1996 | Ray |
| 5,531,746 A | 7/1996 | Errico et al. |
| 5,536,127 A | 7/1996 | Pennig |
| 5,549,612 A | 8/1996 | Yapp et al. |
| 5,558,674 A | 9/1996 | Heggeness et al. |
| 5,578,035 A | 11/1996 | Lin |
| 5,586,985 A | 12/1996 | Putnam et al. |
| 5,591,168 A | 1/1997 | Judet et al. |
| 5,601,553 A | 2/1997 | Trebing et al. |
| 5,603,715 A | 2/1997 | Kessler |
| 5,607,426 A | 3/1997 | Ralph et al. |
| 5,662,655 A | 9/1997 | Laboureau et al. |
| 5,665,086 A | 9/1997 | Itoman et al. |
| 5,665,087 A | 9/1997 | Huebner |
| 5,665,089 A | 9/1997 | Dall et al. |
| 5,669,915 A | 9/1997 | Caspar et al. |
| 5,676,667 A | 10/1997 | Hausman |
| 5,709,682 A | 1/1998 | Medoff |
| 5,709,686 A | 1/1998 | Talos et al. |
| 5,718,705 A | 2/1998 | Sammarco |
| 5,728,099 A | 3/1998 | Tellman et al. |
| 5,733,287 A | 3/1998 | Tepic et al. |
| 5,749,872 A * | 5/1998 | Kyle et al. ................. 606/69 |
| 5,766,174 A | 6/1998 | Perry |
| 5,772,662 A | 6/1998 | Chapman et al. |
| 5,776,194 A | 7/1998 | Mikol et al. |
| 5,785,711 A | 7/1998 | Errico et al. |
| 5,807,396 A | 9/1998 | Raveh |
| 5,851,207 A | 12/1998 | Cesarone |
| 5,853,413 A | 12/1998 | Carter et al. |
| 5,879,350 A | 3/1999 | Sherman |
| 5,931,839 A | 8/1999 | Medoff |
| 5,935,128 A | 8/1999 | Carter et al. |
| 5,938,664 A | 8/1999 | Winquist et al. |
| 5,941,878 A | 8/1999 | Medoff |
| 5,951,557 A | 9/1999 | Luter |
| 5,954,722 A | 9/1999 | Bono |
| 5,964,763 A | 10/1999 | Incavo |
| 5,967,046 A | 10/1999 | Muller |
| 5,968,046 A | 10/1999 | Castleman |
| 5,968,047 A | 10/1999 | Reed |
| 5,989,254 A | 11/1999 | Katz |
| 6,007,535 A | 12/1999 | Rayhack et al. |
| 6,010,503 A | 1/2000 | Richelsoph |
| 6,010,505 A | 1/2000 | Asche et al. |
| 6,022,350 A | 2/2000 | Ganem |
| 6,053,917 A | 4/2000 | Sherman |
| 6,096,040 A | 8/2000 | Esser |
| 6,123,709 A | 9/2000 | Jones |
| 6,129,730 A | 10/2000 | Bono et al. |
| 6,146,384 A | 11/2000 | Lee et al. |
| 6,152,927 A | 11/2000 | Farris et al. |
| 6,183,475 B1 | 2/2001 | Lester et al. |
| 6,197,028 B1 | 3/2001 | Ray et al. |
| 6,206,881 B1 | 3/2001 | Frigg et al. |
| 6,221,073 B1 | 4/2001 | Weiss et al. |
| D443,060 S | 5/2001 | Benirschke et al. |
| 6,228,285 B1 | 5/2001 | Wang et al. |
| 6,231,576 B1 | 5/2001 | Frigg et al. |
| 6,235,033 B1 | 5/2001 | Brace et al. |
| 6,235,034 B1 | 5/2001 | Bray |
| 6,238,395 B1 | 5/2001 | Bonutti |
| 6,241,736 B1 | 6/2001 | Sater et al. |
| 6,248,109 B1 | 6/2001 | Stoffella |
| 6,258,089 B1 | 7/2001 | Campbell et al. |
| 6,270,499 B1 * | 8/2001 | Leu et al. ................. 606/64 |
| 6,283,969 B1 | 9/2001 | Grusin et al. |
| 6,290,703 B1 | 9/2001 | Ganem |
| 6,322,562 B1 | 11/2001 | Wolter |
| 6,355,041 B1 | 3/2002 | Martin |
| 6,355,043 B1 | 3/2002 | Adam |
| 6,358,250 B1 | 3/2002 | Orbay |
| 6,364,882 B1 | 4/2002 | Orbay |
| 6,379,359 B1 * | 4/2002 | Dahners .................. 606/62 |
| 6,383,186 B1 | 5/2002 | Michelson |
| 6,409,768 B1 | 6/2002 | Tepic et al. |
| 6,440,135 B2 | 8/2002 | Orbay et al. |
| 6,454,769 B2 | 9/2002 | Wagner et al. |
| 6,454,770 B1 | 9/2002 | Klaue |
| 6,458,133 B1 | 10/2002 | Lin |
| 6,468,278 B1 | 10/2002 | Muckter |

| | | |
|---|---|---|
| 6,508,819 B1 | 1/2003 | Orbay |
| 6,527,775 B1 | 3/2003 | Warburton |
| 6,540,748 B2 | 4/2003 | Lombardo |
| 6,595,993 B2 | 7/2003 | Donno et al. |
| 6,599,290 B2 | 7/2003 | Bailey et al. |
| 6,602,255 B1 | 8/2003 | Campbell et al. |
| 6,623,486 B1 | 9/2003 | Weaver et al. |
| 6,626,908 B2 | 9/2003 | Cooper et al. |
| 6,645,212 B2 | 11/2003 | Goldhahn et al. |
| 6,669,700 B1 | 12/2003 | Farris et al. |
| 6,679,883 B2 | 1/2004 | Hawkes et al. |
| 6,692,503 B2 | 2/2004 | Foley |
| 6,706,046 B2 | 3/2004 | Orbay et al. |
| 6,712,820 B2 | 3/2004 | Orbay |
| 6,719,758 B2 | 4/2004 | Beger et al. |
| 6,730,090 B2 | 5/2004 | Orbay et al. |
| 6,730,091 B1 | 5/2004 | Pfefferle et al. |
| 6,755,831 B2 | 6/2004 | Putnam |
| 6,761,719 B2 | 7/2004 | Justis et al. |
| 6,767,351 B2 | 7/2004 | Orbay et al. |
| 6,780,186 B2 | 8/2004 | Errico et al. |
| 6,866,665 B2 | 3/2005 | Orbay |
| 6,926,720 B2 | 8/2005 | Castaneda |
| 6,955,677 B2 | 10/2005 | Dahners |
| 6,974,461 B1 | 12/2005 | Wolter |
| 7,090,676 B2 | 8/2006 | Huebner et al. |
| 7,153,309 B2 | 12/2006 | Huebner et al. |
| 2001/0001119 A1 | 5/2001 | Lombardo |
| 2001/0011172 A1 | 8/2001 | Orbay et al. |
| 2001/0021851 A1 | 9/2001 | Eberlein et al. |
| 2002/0032446 A1 | 3/2002 | Orbay |
| 2002/0049445 A1 | 4/2002 | Hall, IV et al. |
| 2002/0058939 A1 | 5/2002 | Wagner et al. |
| 2002/0058941 A1 | 5/2002 | Clark et al. |
| 2002/0111629 A1 | 8/2002 | Phillips |
| 2002/0147452 A1 | 10/2002 | Medoff et al. |
| 2002/0151899 A1 | 10/2002 | Bailey et al. |
| 2002/0156474 A1 | 10/2002 | Wack et al. |
| 2003/0045880 A1 | 3/2003 | Michelson |
| 2003/0078583 A1 | 4/2003 | Biedermann et al. |
| 2003/0083661 A1 | 5/2003 | Orbay et al. |
| 2003/0105461 A1 | 6/2003 | Putnam |
| 2003/0135212 A1 | 7/2003 | Chow |
| 2003/0153919 A1 | 8/2003 | Harris |
| 2003/0216735 A1 | 11/2003 | Altarac et al. |
| 2004/0059334 A1 | 3/2004 | Weaver et al. |
| 2004/0059335 A1 | 3/2004 | Weaver et al. |
| 2004/0068319 A1 | 4/2004 | Cordaro |
| 2004/0073218 A1 | 4/2004 | Dahners |
| 2004/0097934 A1 | 5/2004 | Farris et al. |
| 2004/0102778 A1 | 5/2004 | Huebner et al. |
| 2004/0111090 A1 | 6/2004 | Dahners |
| 2004/0193163 A1 | 9/2004 | Orbay |
| 2004/0260291 A1 | 12/2004 | Jensen |
| 2005/0004574 A1 | 1/2005 | Muckter |
| 2005/0080421 A1 | 4/2005 | Weaver et al. |
| 2005/0131413 A1 | 6/2005 | O'Driscoll et al. |
| 2005/0154392 A1 | 7/2005 | Medoff et al. |
| 2005/0165400 A1 | 7/2005 | Fernandez |
| 2005/0187551 A1 | 8/2005 | Orbay et al. |
| 2006/0004462 A1 | 1/2006 | Gupta |
| 2006/0009771 A1 | 1/2006 | Orbay |
| 2006/0015101 A1 | 1/2006 | Warburton et al. |

FOREIGN PATENT DOCUMENTS

| | | |
|---|---|---|
| CH | 675 531 | 10/1990 |
| CN | 1379642 A | 11/2002 |
| DE | 33 01 298 | 2/1984 |
| DE | 40 04 941 | 8/1990 |
| DE | 195 42 116 A | 5/1997 |
| DE | 196 29 011 | 1/1998 |
| DE | 93 21 544 U1 | 9/1999 |
| DE | 43 43 117 C2 | 11/1999 |
| DE | 20200705 | 3/2002 |
| EP | 0 451 427 A1 | 5/1990 |
| EP | 0689800 | 1/1996 |
| FR | 2855391 | 12/2004 |
| WO | WO 97/47251 | 12/1997 |
| WO | WO 00/04836 | 2/2000 |
| WO | WO 00/36984 | 6/2000 |
| WO | WO 01/19267 A | 3/2001 |
| WO | WO 2004/032751 | 4/2004 |
| WO | WO 2004/096067 | 11/2004 |

OTHER PUBLICATIONS

"Numelock II Polyaxial Locking System," Stryker Corporation, brochure.
"SCS.TM./D Distal Radius Plate System: Dorsal", Avanta 1997.
"SCS.TM./V Distal Radius Plate: Volar", Avanta 1998.
"Smartlock Locking Screw Technology," Stryker Corporation, website description, 2004, www.stryker.lcom.
"Summary of Safety and Effectiveness Information"; Synthes.RTM.; Jul. 29, 1998.
"The Distal Radius Plate Instrument and Implant Set", Technique Guide, SYNTHES.RTM., Paoli, PA 1995.
"The Titanium Distal Radius Plate", Technique Guide, Synthes. RTM., Paoli, PA, 1995.
"Universal Distal Radius System", Stryker Corporation, website description, 2004, www.stryker.com.
"VAL Plate (Volar Angle Locking) for Distal Radius Fractures", US Implants, brochure.
"Volar Peg Plate Insertion Technique", Trimed, Inc., brochure.
"Volar Radius Plate with Angular Stability", I.T.S. (Implant Technology Systems), 510(k) Summary of Safety and Effectiveness, Feb. 6, 2004.
"Volare Winkelstabile Radiusplatte", I.T.S. (Implant Technology Systems), Spectromed, brochure, 2005, Austria.
Moftakhar, Roham, M.D. and Trost, Gregory R., M.D., "Anterior Cervical Plates: A Historical Perspective", Jan. 2004, pp. 1-5.
Nelson, "Volar Plating with Anatomic Placement and Fixed-Angle Screws", Quick Reference Guide for Contours VPS Volar Plate System by Orthofix, May 2005, www.orthofix.com.
Polyaxial and Monoaxial Spinal Screws, XIA.TM. Spinal System, www.osteonics.com/osteonics/spine/xia2.html, Jun. 25, 2002.
Putnam, D. M.D., "Repair and Rehabilitation of Distal Fractures: The Role of Ssubchondral Fixation" at pp. 144-147.

* cited by examiner

INTRAMEDULLARY FIXATION DEVICE FOR METAPHYSEAL LONG BONE FRACTURES

This application is a continuation of U.S. Ser. No. 10/762,695, filed Jan. 22, 2004 now abandoned, which is a continuation-in-part of U.S. Ser. No. 10/315,787, filed Dec. 10, 2002 and now issued as U.S. Pat. No. 6,706,046, which is a continuation-in-part of U.S. Ser. No. 10/159,611, filed May 30, 2002 and now issued as 6,730,090, all of which are hereby incorporated by reference herein in their entireties.

BACKGROUND OF THE INVENTION

1. Field of the Invention

This invention relates broadly to surgical devices. More particularly, this invention relates to a bone fixation system including a plate element and an arrangement of pegs fixed relative to the plate element.

2. State of the Art

Figure 1:
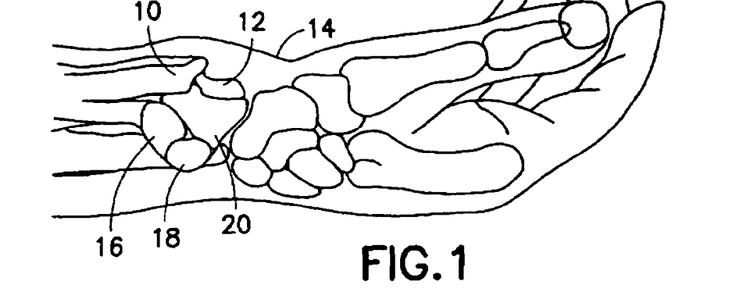
FIG. 1 is an illustration of an extremity subject to a Colles' fracture.

Referring to FIG. 1, a Colles' fracture is a fracture resulting from compressive forces being placed on the distal radius 10, and which causes backward displacement of the distal fragment 12 and radial deviation of the hand at the wrist 14. Often, a Colles' fracture will result in multiple bone fragments 16, 18, 20 which are movable and out of alignment relative to each other. If not properly treated, such fractures result in permanent wrist deformity. It is therefore important to align the fracture and fixate the bones relative to each other so that proper healing may occur.

Alignment and fixation are typically performed by one of several methods: casting, external fixation, interosseous wiring, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Interosseous wiring is an invasive procedure whereby screws are positioned into the various fragments and the screws are then wired together as bracing. This is a difficult and time consuming procedure. Moreover, unless the bracing is quite complex, the fracture may not be properly stabilized. Plating utilizes a stabilizing metal plate typically against the dorsal side of the bones, and a set of parallel pins extending from the plate into holes drilled in the bone fragments to provide stabilized fixation of the fragments. However, the currently available plate systems fail to provide desirable alignment and stabilization. Likewise, other fractures at the ends of other long bones suffer from similar problems.

SUMMARY OF THE INVENTION

It is therefore an object of the invention to provide an improved fixation and alignment system for fractures at the end of long bones and which can specifically be used to treat fractures at the end of long bones.

It is another object of the invention to provide a fixation system which desirably aligns and stabilizes multiple bone fragments in a fracture to permit proper healing.

In accord with these objects, which will be discussed in detail below, a fixation system is provided which generally includes a plate intended to be positioned against the bone, a plurality of bone screws for securing the plate along a non-fractured portion of the bone, and a plurality of pegs (fasteners having threaded heads and threaded or non-threaded shafts) which extend from the plate and into bone fragments of the fracture.

According to one embodiment, the plate is generally a T-shaped plate defining an elongate shaft portion, a head portion angled relative to the shaft portion, a first side which is intended to contact the bone, and a second side opposite the first side. The shaft portion includes a plurality of countersunk screw holes for the extension of the bone screws therethrough. The head portion includes a plurality of threaded peg holes for receiving the pegs therethrough. According to a first embodiment, the peg holes are preferably arranged along a curve. According to a second embodiment, the peg holes are preferably linearly arranged. In either embodiment, the peg holes are preferably positioned increasingly distal in a medial to lateral direction along the second side. According to a preferred aspect of the invention, axes through the peg holes are oblique relative to each other, and are preferably angled relative to each other in two dimensions.

In use for stabilization of Colles' fracture, the plate is positioned with its first side against the volar side of the radius and bone screws are inserted through the bone screw holes into the radius to secure the plate to the radius. The bone fragments are aligned and a drill is used to drill holes into the bone fragments in alignment with the axes of the peg holes. The pegs are then inserted through the peg holes and into the holes in the bone, and the heads of the pegs are threadably engaged in the head portion of the plate. The pegs define a support framework which is preferably divergent both medial and laterally such that the pegs are arranged to follow the contour of subchondral bone of the bone being stabilized. The fixation system thereby secures the bone fragments in their proper orientation.

According to another embodiment, a fixation system includes a device having a proximal shaft portion defining an intramedullary nail and relatively flat plate head portion, preferably horizontally and vertically offset relative to the shaft portion by a neck portion. The shaft portion includes screw holes, and the plate portion has a low, narrow profile and includes longitudinally displaced peg holes, each of which is adapted to orient a peg in a different orientation from the others.

In use, a relatively small incision is made in the skin, and the shaft portion is introduced through the incision and through the fracture location into the medullary canal of the bone, and the plate portion of the device is maneuvered against a surface of the bone at the metaphysis. The shaft portion is fixed relative to the bone with one or more screws, while pegs are inserted through holes drilled in alignment with the peg holes and define a framework for stabilization and support of subchondral bone fragments. Moreover, as the pegs preferably enter the subchondral fragments from a plurality of directions, additional fixation of the device into the bone is provided.

The fixation system can be adapted to treatment of fractures at multiple sites. For example, the distal radius, the proximal humerus, the distal femur, the proximal tibia, the distal tibia, and the hip are all suitable for application of the system of the invention.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 2:
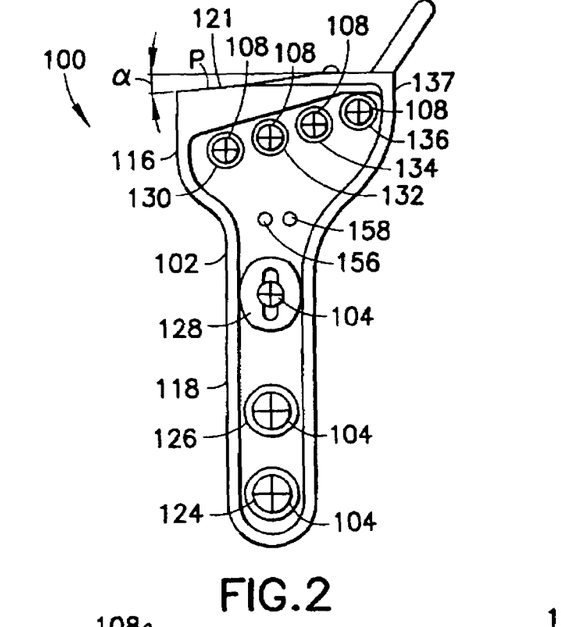
FIG. 2 is a top volar view of a fixation system specifically adapted for a distal radius fracture according to a first embodiment of the invention.
Figure 3:
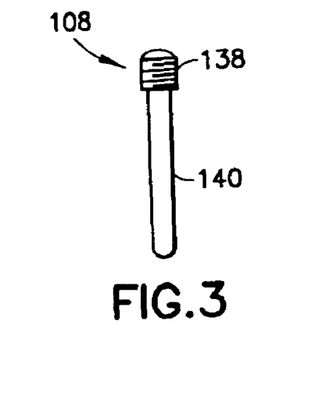
FIG. 3 is a side view of a peg with a non-threaded shaft according to an embodiment of the fixation system of the invention.
Figure 3A:
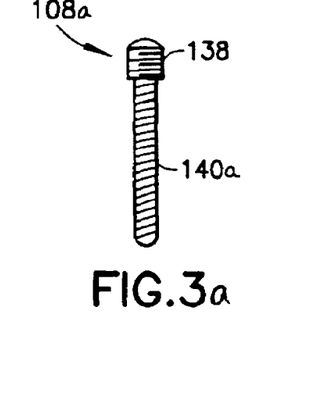
FIG. 3a is a side view of a peg with a threaded shaft according to an embodiment of the fixation system of the invention.
Figure 4:
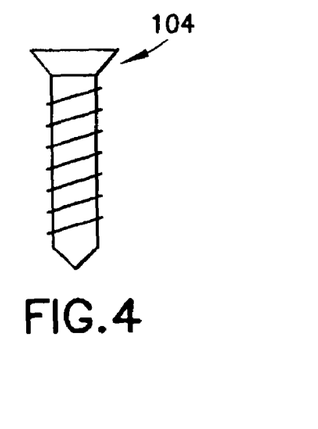
FIG. 4 is a side view of a bone screw of an embodiment of the fixation system of the invention.

Turning now to FIGS. 2 through 4, a first embodiment of a fixation system 100 for aligning and stabilizing multiple bone fragments in a Colles' fracture generally includes a substantially rigid T-shaped plate 102 intended to be positioned against the volar side of the radial bone, a plurality of preferably self-tapping bone screws 104 for securing the plate 102 along a non-fractured portion of the radial bone, and a plurality of bone pegs 108, 108a which extend from the plate 102 and into bone fragments of a Colles' fracture.

Figure 5:
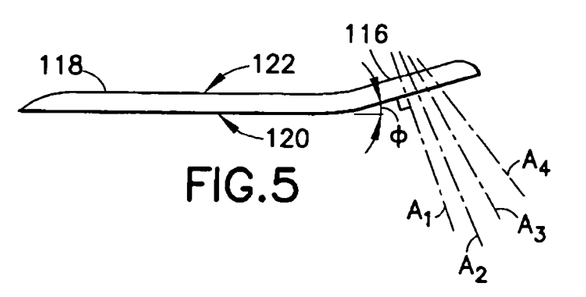
FIG. 5 is a side view of an embodiment of the fixation system of the invention.
Figure 6:
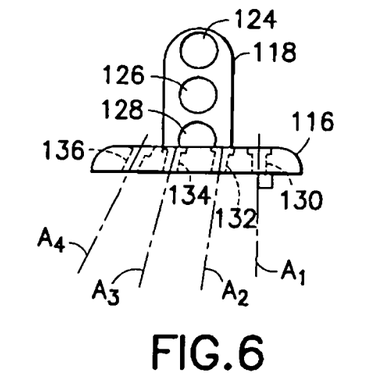
FIG. 6 is a front end view of an embodiment of the volar fixation system of an embodiment of the invention.

Referring to FIGS. 2, 5 and 6, more particularly, the T-shaped plate 102 defines a relatively flat head portion 116 angled upwards relative to an elongate relatively flat shaft portion 118, a first side 120 which is intended to contact the bone, and a second side 122 opposite the first side. As the head portion and shaft portion are angled relative to each other, the first side preferably generally defines two planar portions. The angle $\phi$ between the head portion 116 and the shaft portion 118 is preferably approximately 18° and bent at a radius of approximately 1.00 inch (FIG. 5). The distal edge 121 of the head portion 116 is preferably angled proximally toward the medial side at an angle a, e.g., 5°, relative to a line P, which is perpendicular to the shaft portion. In one embodiment, the head portion 116 preferably has a width of 0.913 inch and a greatest proximal-distal dimension (i.e., from the corner of angle $\alpha$ to the shaft portion) of approximately 0.69 inch, and the shaft portion preferably has a width of 0.375 inch and a length of 1.40 inches, though alternative dimensions may be provided for plates adapted for various individuals, or for plates adapted for use on bones other than the radius. The plate 102 preferably has a thickness of at least approximately 0.098 inch. The plate 102 is preferably made from a titanium alloy, such as Ti-6A-4V.

The shaft portion 118 includes three preferably countersunk screw holes 124, 126, 128 for the extension of the bone screws 104 therethrough. One of the screw holes, 128, is preferably generally elliptical (or oval).

The head portion 116 includes four threaded peg holes 130, 132, 134, 136 for individually receiving the pegs 108, 108a therethrough. According to a first preferred aspect of the first embodiment of the invention, the peg holes 130, 132, 134, 136, each preferably 0.100 inch in diameter, are preferably substantially linearly arranged along the head portion 116, and are provided such that the adjacent peg holes are provided further distally in a medial to lateral direction along the second side. Alternatively, the peg holes may be arranged along a smooth curve such as a shallow parabolic curve.

The peg holes define axes $A_1, A_2, A_3, A_4$ which are oblique (not parallel) relative to each other, and more preferably are angled in two dimensions (medial/lateral and proximal/distal) relative to each other; i.e., the pegs once inserted into the peg holes are also angled in two dimensions relative to each other. More particularly, the first axis $A_1$ of the first peg hole 130 (that is, the most proximal and medial peg hole) is preferably directed normal to the first side 120 of the head portion 116. The axis $A_2$ of the adjacent peg hole 132, i.e., the second axis, is preferably angled approximately 1-7° distal and lateral relative to the first axis $A_1$, and more preferably approximately 2.5° distal and lateral relative to the first axis $A_1$. The axis $A_3$ of the peg hole 134 laterally adjacent the second peg hole 132, i.e., the third axis, is preferably angled approximately 7-13° distal and lateral relative to the first axis $A_1$, and more preferably approximately 10° distal and lateral relative to the first axis $A_1$. The axis $A_4$ of the peg hole 134 laterally adjacent the third peg hole 132, i.e., the fourth axis, is preferably angled approximately 10-30° distal and lateral relative to the first axis $A_1$, and more preferably approximately 20° distal and lateral relative to the first axis $A_1$. The second side of the head portion 116, distal of the peg holes 130, 132, 134, 136 is preferably beveled.

Referring back to FIGS. 3 and 3a, the pegs 108, 108a, preferably approximately 0.872 inch in length, each have a threaded head 138 adapted to threadably engage the threads about the threaded peg holes 130, 132, 134, 136. Such dimensions permit the pegs to adequately support the bone fragments such that the bone is able to heal correctly. The pegs may have a relatively smooth shaft 140 (FIG. 3) or a threaded shaft (FIG. 3a). If threaded, the shafts 140a are preferably threaded at a pitch different from the threads on the head 138 of the pegs 108a. The pegs 108 are also preferably made from titanium alloy, and may be coated in a ceramic, e.g., titanium nitride, to provide a bone interface which will not adversely affect bone healing.

Figure 7:
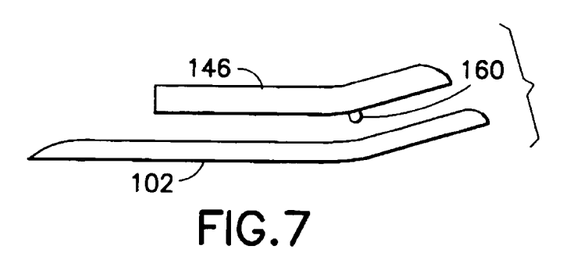
FIG. 7 is an exploded side view of the right hand volar plate and guide plate according to the first embodiment of the fixation system of the invention.
Figure 8:
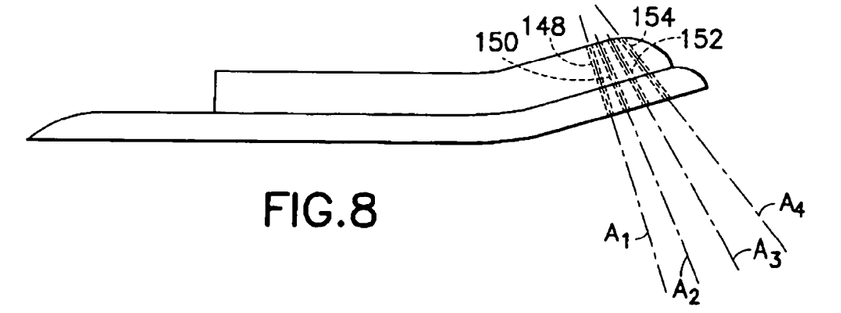
FIG. 8 is a side view of the guide plate positioned on the right hand volar plate to provide drill guide paths in accord with the invention.
Figure 9:
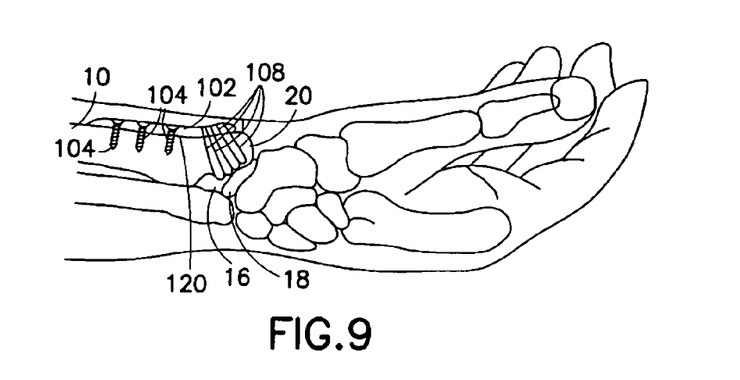
FIG. 9 is an illustration of the first embodiment of the volar fixation system provided in situ aligning and stabilizing a Colles' fracture.

Turning now to FIGS. 7 and 8, the system 100 may also include a guide plate 146 which temporarily sits on the second side 122 of the volar plate 102 and includes guide holes 148, 150, 152, 154 (illustrated in overlapping section in FIG. 8) oriented according to the axes $A_1, A_2, A_3, A_4$ of the peg holes for guiding a drill into the bone fragments at the required orientation. That is, the guide holes together with the peg holes define a drill guide path along the axes with sufficient depth to accurately guide a drill (not shown) to drill holes at the desired pin orientations. The volar plate 102 and guide plate 146 are also preferably provided with mating elements, such as a plurality of holes 156, 158 on the second side of the volar plate (FIG. 2), and a plurality of protuberances 160 on the mating side of the guide plate (FIG. 7), to temporarily stabilize the guide plate on the volar plate during the hole drilling process. Alternatively, a threaded drill guide or other guide means may be used to guide a drill to drill holes in appropriate orientations relative to the peg hole axes, as is known in the art.

Referring to FIGS. 2 through 9, in use, the volar plate 102 is positioned with its first side 120 against the volar side of the radius. Bone screws 104 (either self-tapping or inserted with the aid of pre-drilled pilot holes) are inserted through the bone screw holes 124, 126, 128 into the radius bone 10 to secure the volar plate 102 to the radius. The bone fragments 16, 18, 20 are then aligned with the radius 10. Next, the guide plate 146 is positioned on the second side of the volar plate. A drill, guided by a guide path formed by the peg holes and the guide holes, drills holes into and between the bone fragments 16, 18, 20 (and possibly also a portion of the integral radius, depending upon the particular location and extent of the fracture), and the guide plate is then removed. The pegs 108, 108a (any combination thereof including solely non-threaded shaft pegs 108 and solely threaded shaft pegs 108a) are then inserted through the peg holes 130, 132, 134, 136 and into the holes drilled into the fragments, and the heads of the pegs are threadably engaged in the volar plate. The pegs 108, 108a, extending through the oblique-axis peg holes 130, 132, 134, 136, are positioned immediately below the subchondral bone of the radius and support the bone fragments for proper healing. The volar fixation system thereby secures the bone fragments in their proper orientation.

Figure 10:
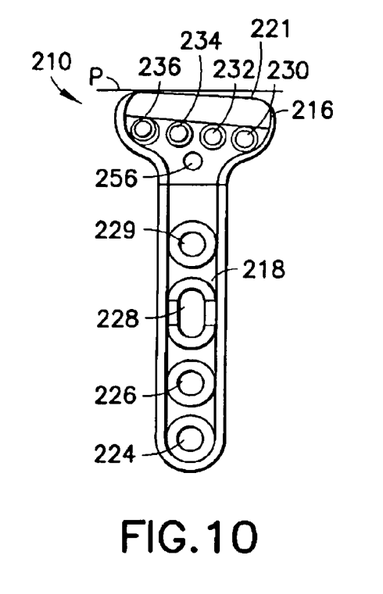
FIG. 10 is a top volar view of a left hand volar fixation system according to the second embodiment of the invention.
Figure 11:
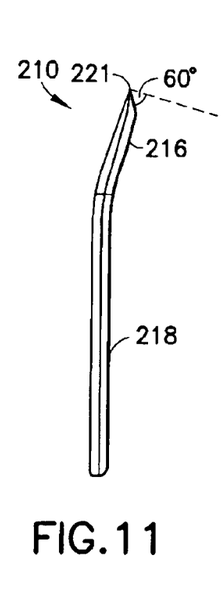
FIG. 11 is a lateral side view of the left hand volar fixation system according to the second embodiment of the invention.
Figure 12:
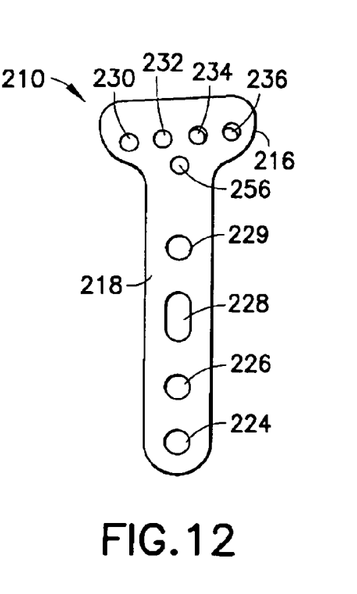
FIG. 12 is a bottom view of the left hand volar fixation system according to the second embodiment of the invention.

Referring to FIGS. 10-12, a second embodiment of a volar plate 210, substantially similar to the first embodiment (with like parts having numbers incremented by 100) and used in substantially the same manner as the first embodiment is shown. The plate 210 preferably has a length of approximately 2.35 inches, which is approximately 0.35 inch greater than in the first embodiment. This additional length accommodates an extra bone screw hole 229 in the shaft portion of the volar plate such that the volar plate preferably includes four bone screw holes 224, 226, 228, 229. The additional bone screw in screw hole 229 increases plate stability over the three holes of the first embodiment. The plate 210 preferably tapers in thickness from the shaft portion 218 to the head portion 216. A preferred taper provides a proximal shaft portion 218 thickness of approximately 0.098 inch and head portion 216 thickness of approximately 0.078 inch. The taper decreases the thickness of the head portion 216 relative to the shaft portion such that the weight of the volar plate is reduced and an improved tendon clearance is provided. The distal edge of the head portion 216 has an increased taper (preferably approximately 60° relative to a line normal to the head) to a distal edge 221. The edge 221 is broken (i.e., made blunt) to prevent irritation or disturbance to the surrounding anatomy.

The head portion 216 includes four threaded peg holes 230, 232, 234, 236 for individually receiving pegs 208 therethrough (FIGS. 13 and 14), and a guide hole 256 for alignment of a guide plate. According to a preferred aspect of the second embodiment of the invention, the peg holes 230, 232, 234, 236, preferably 0.100 inch in diameter, are preferably linearly arranged along the head portion 216, and are provided such that the adjacent peg holes are provided further distally in a medial to lateral direction along the first and second sides. Referring to FIG. 15, more particularly, according to a preferred dimensions of the second embodiment of the invention, the center of peg hole 230 is located approximately 0.321 inch proximal line P and approximately 0.750 inch medial of the lateral edge 237 of the head portion, the center of peg hole 232 is located approximately 0.306 inch proximal line P and 0.557 inch medial of the lateral edge 237, the center of peg hole 234 is located approximately 0.289 inch proximal line P and approximately 0.364 inch medial of the lateral edge 237, and the center of peg hole 236 is located approximately 0.272 inch proximal line P and approximately 0.171 inch medial of the lateral edge 237. As such, the distance from each of the peg holes to the distal edge 221 of the volar plate is relatively greater than in the first embodiment, and provides a preferred alignment with respect to the tapered distal edge 221.

Referring to FIGS. 15-24, in addition, as in the first embodiment, the peg holes define axes $A_1, A_2, A_3, A_4$ which are oblique relative to each other, and more preferably are angled in two dimensions (medial/lateral and proximal/distal) relative to each other; i.e., the pegs 208 once inserted into the peg holes are also angled in two dimensions relative to each other. More particularly, as in the first embodiment, the first axis $A_1$ of the first peg hole 230 is preferably directed normal (FIGS. 16 and 21) to the first side 220 of the head portion 216. The axis $A_2$ of peg hole 232 is preferably angled approximately 1-7° distal (FIG. 17) and approximately 1-7° lateral (FIG. 22) relative to the axis $A_1$, and more preferably approximately 2.5° both distal and lateral relative to axis $A_1$. The axis $A_3$ of peg hole 234 is preferably angled approximately 7-13° distal (FIG. 18) and approximately 7-13° lateral (FIG. 23) relative to axis $A_1$, and more preferably approximately 10° both distal and lateral relative to axis $A_1$. Axis $A_4$ of the peg hole 234 is preferably angled approximately 10-30° distal (FIG. 19) and approximately 10-30° lateral (FIG. 24) relative to axis $A_1$, and more preferably approximately 20° both distal and lateral relative to axis $A_1$.

Referring to FIGS. 13 and 16-19, each of the peg holes has a countersunk portion 270, 272, 274, 276, respectively, for receiving the head 238 of peg 208. Countersunk portions 270, 272 are each preferably approximately 0.030 inch deep and threaded according to the head of the pegs, as described below. Countersunk portion 274 is preferably approximately 0.042 inch deep and likewise threaded. Countersunk portion 276 is preferably approximately 0.056 inch deep and also threaded. The respective depths of the countersunk portions are adapted to better accommodate the heads 238 of the pegs 208 relative to the respective axes of the peg holes.

Figure 13:
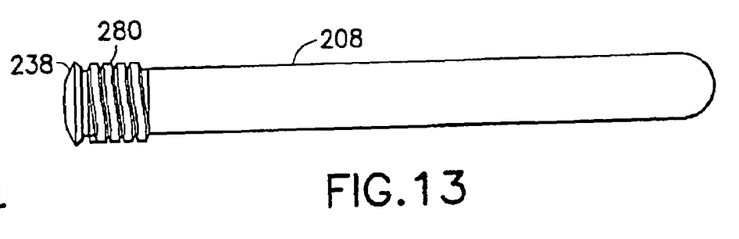
FIG. 13 is an enlarged side elevation of a bone peg according to the second embodiment of the volar fixation system of the invention.
Figure 14:
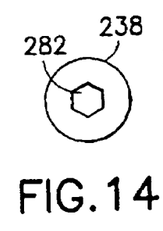
FIG. 14 is a proximal end view of the bone peg of FIG. 13.
Figure 15:
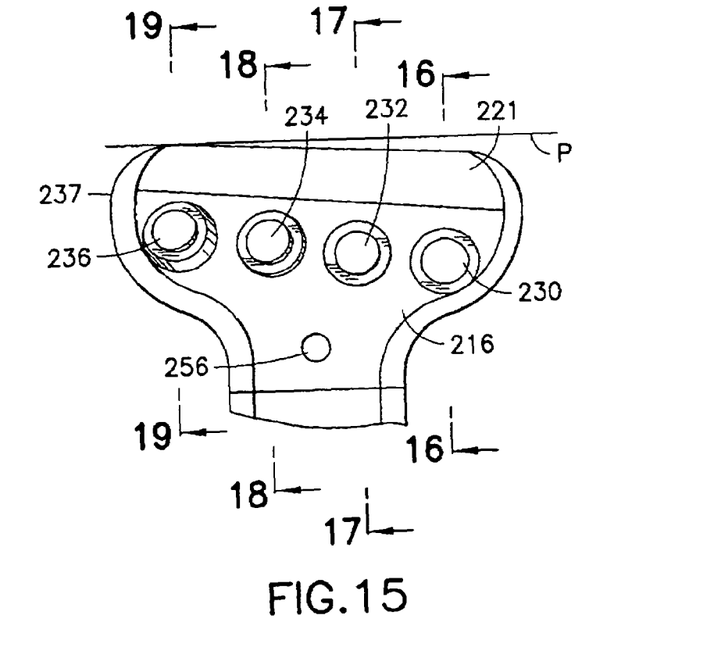
FIG. 15 is first partial top view of the head portion of the left hand volar plate according to the second embodiment of the volar fixation system of the invention.
Figure 16:
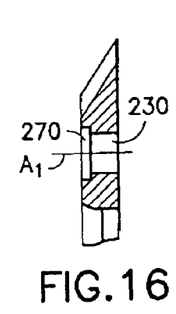
FIGS. 16-19 are section views across line 16-16, 17-17, 18-18, and 19-19, respectively in FIG. 15.
Figure 17:
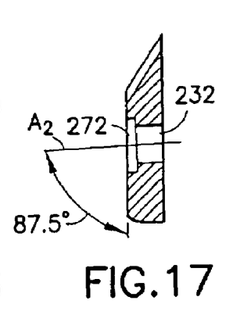
Figure 18:
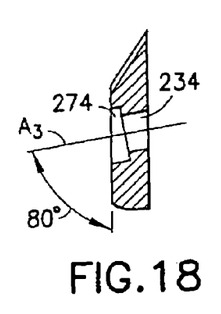
Figure 19:
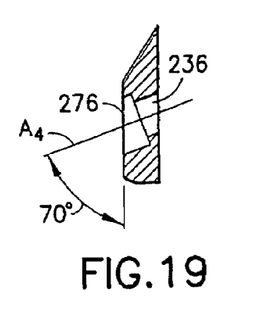
Figure 20:
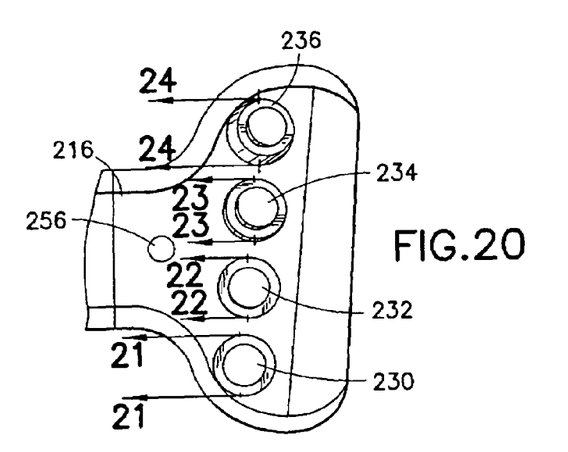
FIG. 20 is second partial top view of the head portion of the left hand volar plate according to the second embodiment of the volar fixation system of the invention.
Figure 21:
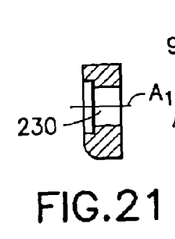
FIGS. 21-24 are section views across line 21-21, 22-22, 23-23, and 24-24, respectively in FIG. 20.
Figure 22:
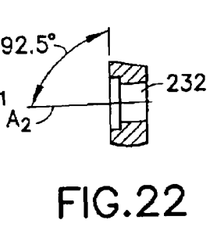
Figure 23:
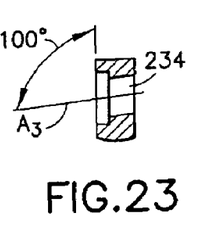
Figure 24:
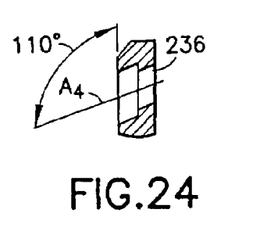

Referring to FIGS. 13 and 14, the pegs 208, preferably approximately 0.872 inch in length, each have a threaded head 238 adapted to threadably engage threads about the peg holes 230, 232, 234, 236 and cylindrical shaft 240 which may be threaded or non-threaded. The heads 238 preferably include a no. 5 thread 280 at a count of 44 per inch. In addition, the heads 238 are rounded and include a hex socket 282 to facilitate stabilized threading into the peg holes. This design accommodates the reduced thickness of the volar plate at the head portion 216. The shafts 240 are preferably approximately 0.0792 inch (2 mm) in diameter and 0.765 inch in length. Such dimensions permit the pegs to adequately support the bone fragments such that the bone is able to heal correctly. The pegs 208 are also preferably made from titanium alloy, and are preferably 'tiodized' to provide a strong finish which does not adversely affect bone healing.

From the foregoing embodiments, it is appreciated that the peg holes define a plurality of axes at least two of which are oblique relative to each other and at least one of which is oblique relative to the lower surface of the head of the plate immediately surrounding such hole. In addition, the threaded peg holes define axes which diverge in a direction away from the lower surface of the plate. As such, pegs coupled within such holes define a support framework which is preferably divergent both medial and laterally such that the pegs are arranged to follow the contour of subchondral bone of the bone being stabilized.

Furthermore, the head portion provides substantial support structure both proximal and distal of the threaded holes for supporting the bone fragments. So that substantial surface structure of the plate is provided for the support, preferably the peg holes define less than fifty percent of the area of the head portion, as clearly shown in FIGS. 2 and 15. Furthermore, as also shown in the embodiment of FIG. 15, a greater area of the head portion is preferably provided distal of the arrangement of the peg holes (on the side of the pegs holes opposite the shaft portion) relative to the area on the head portion proximal of the arrangement of peg holes (on the portion of the head portion adjacent the shaft portion). This large distal area provides a buttress for supporting bone fragments thereunder.

Figures 25, 26, 27, 28:
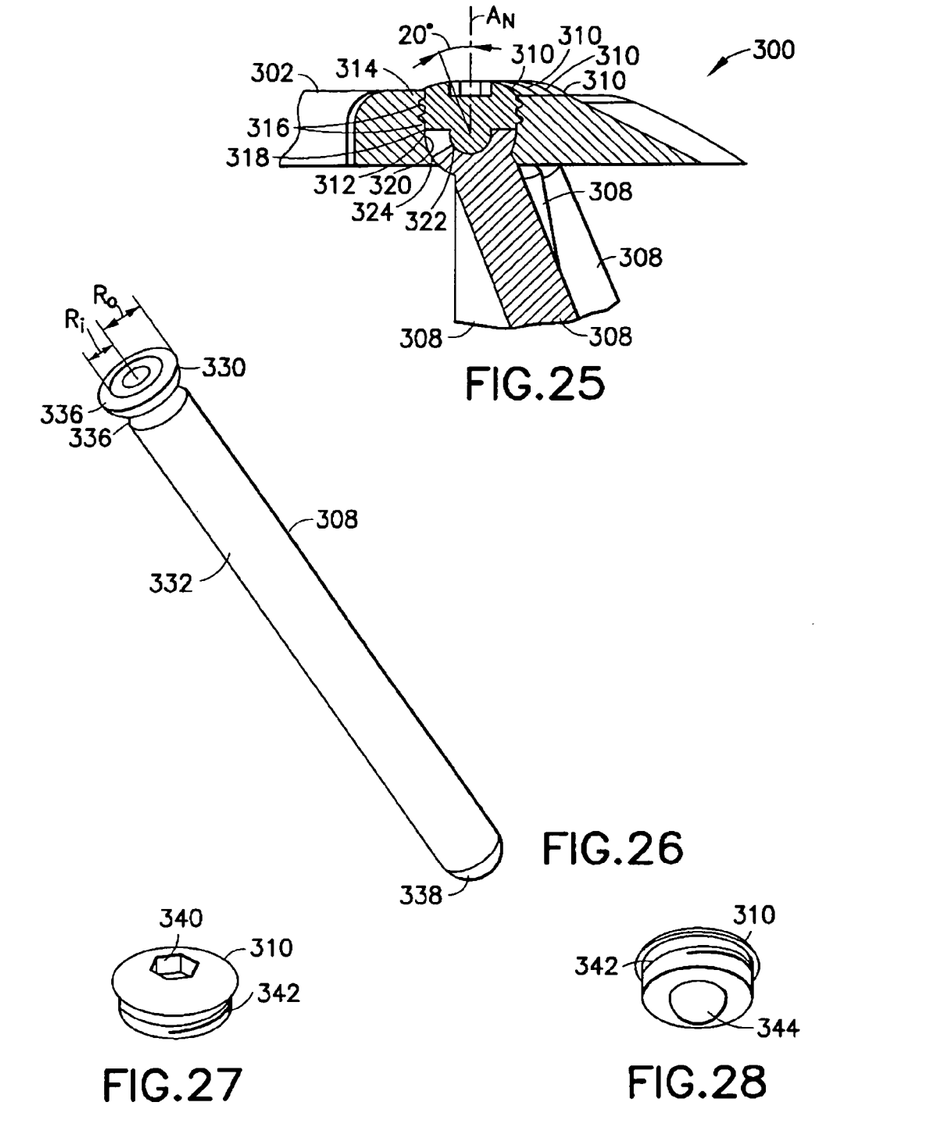
FIG. 25 is a broken partial longitudinal section view across a distal end of a third embodiment of the volar fixation system of the invention.
FIG. 26 is a proximal perspective view of a bone peg according to the third embodiment of the invention.
FIGS. 27 and 28 are proximal and distal perspective views, respectively, of a set screw according to the third embodiment of the invention.
Figures 29, 30, 31:
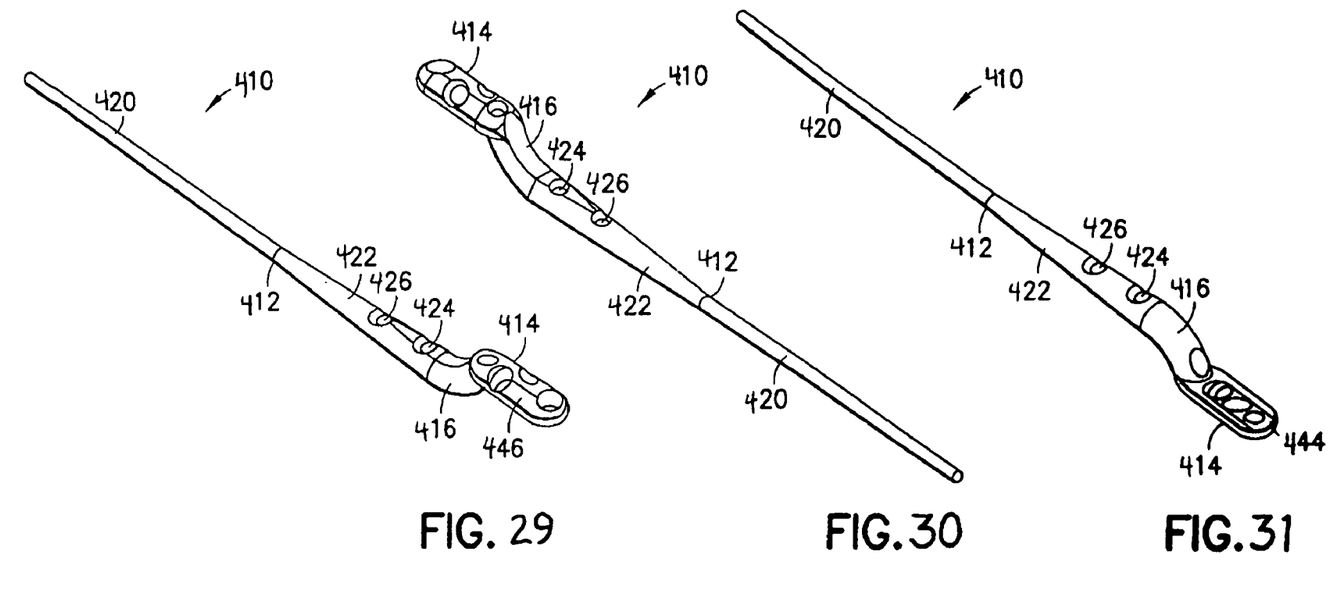
FIG. 29 is a distal end top perspective view of a fourth embodiment of a fixation device of the invention.
FIG. 30 is a proximal end top perspective view of the fixation device of FIG. 29.
FIG. 31 is a distal end bottom perspective view of the fixation device of FIG. 29.

Turning now to FIG. 25, a volar fixation system 300 according to a third embodiment is shown in which each peg can be articulated through a range of angles within a respective peg hole and fixed at a desired angle within the range. The system includes a volar plate 302, four pegs 308, and four set screws 310, as well as bone screws, not shown but described above, for mounting the volar plate to the radius.

The volar plate 310 is substantially similar to the first or second embodiments, with the exception of the shape of the peg holes described below, and is used in substantially the same manner as the first embodiment. Each peg hole 312 in the volar plate includes a cylindrical upper bore 314 provided with threads 316 and a lower portion 318 having a radius of curvature. The surface 320 of the lower portion and/or the surface 330 of the head of the peg is preferably roughened, e.g., by electrical, mechanical, or chemical abrasion, or by the application of a coating or material having a high coefficient of friction. The lower opening 322 of each peg hole includes a circumferential bevel 324.

Referring to FIGS. 25 and 26, each peg 308 includes a head 330 and a cylindrical shaft 332. The proximal portion 334 of the head 330 includes a cup 336 having an outer radius $R_o$ substantially corresponding to the radius of the lower portion 318 of the peg holes 312, and a relatively smaller inner radius $R_i$ of curvature. The head 330 defines preferably approximately 160° of a sphere. The shaft 332 includes a slight taper 336 at the intersection with the head 330, and a rounded distal end 338. According to a preferred manufacture of the pegs 308, the cylindrical shaft 332 is first provided with a sphere (not shown) or a hemisphere (not shown) at a proximal end. If a sphere is provided, it is cut to a hemisphere. The hemisphere is then hollowed and further reduced to the 160° shape. Finally, the taper 336 is provided at the intersection.

Turning now to FIGS. 25, 27 and 28, each set screw 310 includes a proximal hex socket 340, circumferential threads 342 adapted to engage the threads 316 of the upper bore 314 of the peg hole, and distal hemispherical portion 344 having substantially the same radius of curvature as the inner radius of curvature of the cup 336, and preferably substantially smaller than a radius of the peg holes 312.

In accord with the third embodiment, the volar plate is positioned on the radius, a hole is drilled through the elliptical screw hole on the volar plate and into the radius. A bone screw is inserted through the plate and into the bone. The fractured bones are adjusted under the plate into their desired stabilized positions, and the bone screw is tightened. Then, through the peg holes, the surgeon drills holes into the bone for the stabilization pegs. Unlike the previous embodiments, the holes may be drilled at any angle within a predefined range, and preferably at any angle within a range of 20° relative to an axis normal $A_N$ to the lower surface of the head of the volar plate. Each hole may be drilled at the same angle or at relatively different angles. After each hole is drilled, a peg 308 is inserted therein. The bevel 324 at the lower end 322 of the peg hole 312 and the taper 336 on the shaft cooperate to permit the peg to be oriented with greater angularity relative to the axis $A_N$, if required, as interference between the peg hole and peg shaft is thereby reduced. Once the peg 308 has been appropriately positioned within the peg hole, one of the set screws 310 is threaded into the upper bore 314 of the peg hole 312. The hemispherical portion 344 contacts the head 330 of the peg, seating in the concavity of the cup 336. As the set screw 310 is tightened, the head of the peg, which may be roughened, is sandwiched between the set screw and the roughened inner surface of the lower portion of the peg hole, thereby securing the peg in the selected orientation. The other pegs are similarly positioned and angularly fixed.

Turning now to FIGS. 29 through 33, a fixation device 410 for the treatment of a fracture at an end of a long bone, i.e., a metaphyseal fracture, is provided. The device 410 is preferably made of metal, e.g., titanium or stainless steel, and includes an intramedullary nail shaft portion 412 and a plate-like head portion 414 that is preferably horizontally and vertically offset relative to the shaft portion at a neck portion (or transition zone) 16. As such, the shaft portion 412 and the head portion 414 are fixed in a parallel, but non-coaxial relationship, with the head portion 414 longitudinally displaced relative to the shaft portion 412.

Figure 32:
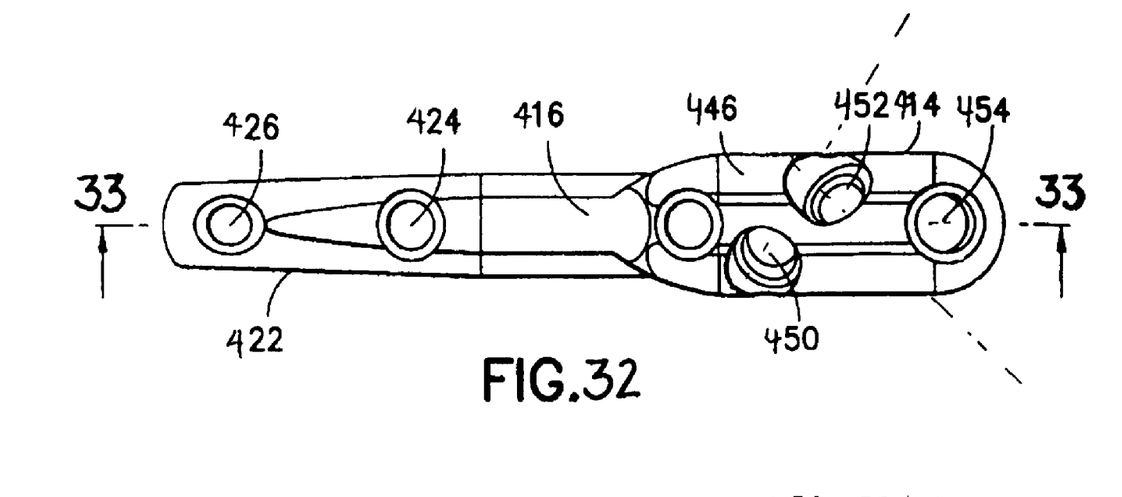
FIG. 32 is a broken top view of the fixation device of FIG. 29.
Figure 33:
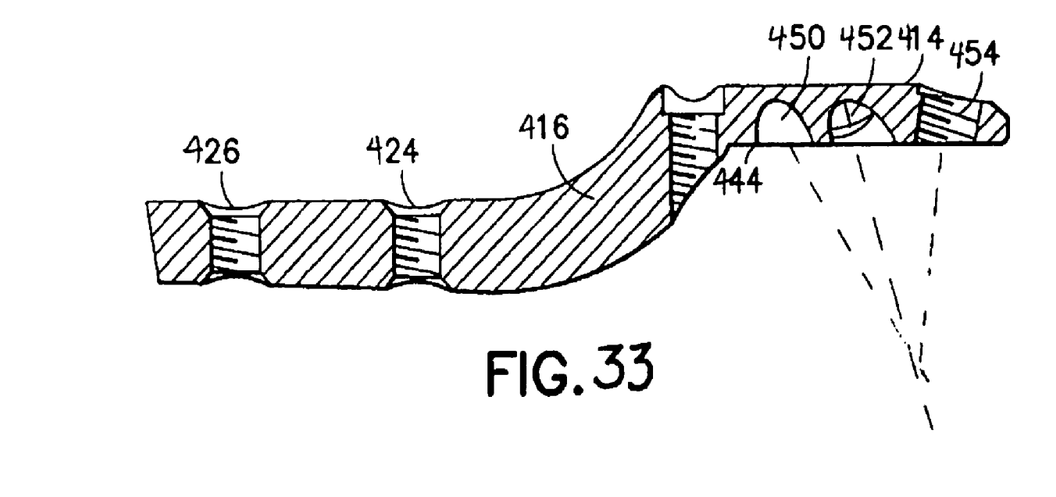
FIG. 33 is a broken longitudinal section view taken along line 33-33 in FIG. 32.

The shaft portion 412 is preferably substantially circular in cross section and includes a tapered resilient (flexible) section 420, and a relatively rigid section 422 generally substantially larger in diameter adjacent the shoulder portion 416. The rigid section 422 preferably tapers toward and into the resilient section 420. Referring to FIGS. 32 and 33, the rigid section 422 of the shaft portion 412 preferably includes two optionally threaded screw holes 424, 426 preferably extending vertically through the diameter of the shaft portion 412 and longitudinally displaced along the length of the rigid section 422. The screw holes 424, 426, if threaded are adapted to receive machine screws as described in detail in U.S. Pat. No. 6,706,046, and if not threaded are adapted to receive cortical screws, as described in detail in U.S. Pat. No. 6,730,090, both of which are hereby incorporated by reference herein in their entireties.

With respect to FIGS. 29 through 33, the plate-like head portion 414 is substantially rigid and has a low and narrow profile. The head portion 414 has a slightly concave bottom surface 444 (adapting the head portion to the anatomy) and a slightly convex upper surface 446 (reducing potential irritation of tendons and other tissue). The concave and convex surfaces 444 and 446 may be defined by facets approximating curved surfaces. The head portion 414 also includes preferably three longitudinally displaced, threaded peg holes 450, 452, 454, each of which is preferably adapted to orient a respective peg (e.g., pegs 108 and 108a of FIGS. 3 and 3a) in a different orientation from the others; i.e., the axes of the peg holes are oblique relative to each other so that the pegs inserted therethrough diverge away from the bottom surface 444 and define a framework under the subchondral surface which supports the fracture. In use, the shaft portion 412 of the device 410 is inserted in the intramedullary canal and the plate-like head portion 414 is provided external of the bone, as described in detail in previously incorporated U.S. Pat. Nos. 6,706,046 and 6,730,090.

There have been described and illustrated herein embodiments of an orthopedic fixation system suitable for numerous applications related to the fixation of various bone fractures. While embodiments of the invention have been described, it is not intended that the invention be limited thereto, as it is intended that the invention be as broad in scope as the art will allow and that the specification be read likewise. Thus, while in one embodiment a volar plate for fixation of a fracture at the distal radius has been shown and described, it is appreciated that a plate with divergent threaded peg holes may be optimized in shape and size for placement on the dorsal radius or for fractures of other bones, such as of the ulna, humerus, femur, tibia, fibula, adjacent the ankle joint, etc. Furthermore, while particular materials for the elements of the system have been disclosed, it will be appreciated that other materials may be used as well. In addition, fewer or more peg holes and pegs than shown may be used, preferably such that at least two pegs angled in two dimensions relative to each other are provided. Also, while a right-handed volar plate for the distal radius is described with respect to an embodiment of the invention, it will be appreciated that both right- and left-handed models are intended, with such alternate models being mirror images of each other. Also, the plate, nail-plate device, and pegs may be provided in different sizes adapted for implant into different size people. It will therefore be appreciated by those skilled in the art that yet other modifications could be made to the provided invention without deviating from its spirit and scope as claimed.

What is claimed is:

1. A bone fracture fixation device for a long bone having a metaphysis with an exterior surface and a diaphysis with a medullary canal, comprising:
   a) an elongate intramedullary nail portion having a circular cross section and including a relatively flexible section and a relatively rigid section relatively larger in diameter than said relatively flexible section, said rigid section including at least one screw hole;
   b) a plate portion having a bone contacting lower surface and including a plurality of fastener holes each structured to constrain an associated fastener at a fixed angle relative to said plate portion, said fixed angles being oblique relative to each other so as to direct associated fasteners in a relatively divergent orientation, wherein said plate portion is not coaxial with said nail portion; and
   c) a neck portion joining said relatively rigid section of said nail portion and said plate portion, said neck portion longitudinally and laterally offsetting said plate portion relative to said nail portion,
      wherein when the nail portion is implanted in the medullary canal of the diaphysis of the long bone, the neck portion offsets the lower surface of said plate so that the lower surface of the plate contacts the exterior surface of the metaphysis of the long bone.

2. A bone fracture fixation device according to claim 1, wherein:
   said plate portion is substantially parallel to said nail portion.

3. A bone fracture fixation device according to claim 1, wherein:
   said relatively rigid section of said nail portion is substantially straight.

4. A bone fracture fixation device according to claim 1, wherein:
   said relatively flexible section is sized to be inserted into a medullary canal of a radius bone.

5. A bone fracture fixation device according to claim 1, wherein:
   said relatively rigid section tapers in diameter into said flexible portion.

6. A bone fracture fixation device according to claim 1, wherein:
   said lower surface of said plate portion is substantially concave.

7. A bone fracture fixation device according to claim 1, wherein:
   said plate portion includes a substantially convex upper surface.

* * * * *